(12) United States Patent
Angeletakis

(10) Patent No.: US 7,683,148 B2
(45) Date of Patent: *Mar. 23, 2010

(54) METATHESIS-CURABLE COMPOSITION WITH A REACTION CONTROL AGENT

(75) Inventor: Christos Angeletakis, Orange, CA (US)

(73) Assignee: Kerr Corporation, Orange, CA (US)

( * ) Notice: Subject to any disclaimer, the term of this patent is extended or adjusted under 35 U.S.C. 154(b) by 936 days.

This patent is subject to a terminal disclaimer.

(21) Appl. No.: 11/428,105

(22) Filed: Jun. 30, 2006

(65) Prior Publication Data

US 2006/0241257 A1 Oct. 26, 2006

Related U.S. Application Data

(63) Continuation-in-part of application No. 10/891,918, filed on Jul. 15, 2004, now Pat. No. 7,173,097, which is a continuation-in-part of application No. 10/430,592, filed on May 6, 2003, now Pat. No. 7,060,770, and a continuation-in-part of application No. 10/430,953, filed on May 6, 2003, now Pat. No. 6,844,409.

(51) Int. Cl.
C08F 4/80 (2006.01)

(52) U.S. Cl. .................. 526/171; 526/128; 526/280; 526/281

(58) Field of Classification Search ............... 526/171, 526/280, 281, 128
See application file for complete search history.

(56) References Cited

U.S. PATENT DOCUMENTS

| | | | |
|---|---|---|---|
| 4,717,498 A | 1/1988 | Maxon | |
| 4,849,127 A | 7/1989 | Maxon | |
| 5,198,511 A | 3/1993 | Brown-Wensley et al. | |
| 5,266,670 A | 11/1993 | Nakos et al. | |
| 5,296,566 A * | 3/1994 | Brown-Wensley et al. | .. 526/171 |
| 5,312,881 A | 5/1994 | Marks et al. | |
| 5,330,948 A | 7/1994 | Marks et al. | |
| 5,455,317 A | 10/1995 | Marks et al. | |
| 5,491,206 A | 2/1996 | Brown-Wensley et al. | |
| 5,728,785 A | 3/1998 | Grubbs et al. | |
| 5,831,108 A | 11/1998 | Grubbs et al. | |
| 5,939,504 A | 8/1999 | Woodson, Jr. et al. | |
| 5,942,638 A | 8/1999 | Lichtenhan et al. | |
| 6,001,909 A | 12/1999 | Setiabudi | |
| 6,040,363 A | 3/2000 | Warner et al. | |
| 6,071,459 A | 6/2000 | Warner et al. | |
| 6,075,068 A | 6/2000 | Bissinger | |
| 6,077,805 A | 6/2000 | Van Der Schaaf et al. | |
| 6,121,362 A | 9/2000 | Wanek et al. | |
| 6,252,101 B1 | 6/2001 | Herzig et al. | |
| 6,306,987 B1 | 10/2001 | Van Der Schaaf et al. | |
| 6,310,121 B1 | 10/2001 | Woodson, Jr et al. | |
| 6,323,296 B1 | 11/2001 | Warner et al. | |
| 6,403,522 B1 | 6/2002 | Bolm et al. | |
| 6,407,190 B1 | 6/2002 | Van Der Schaaf et al. | |
| 6,409,875 B1 | 6/2002 | Giardello et al. | |
| 6,410,666 B1 | 6/2002 | Grubbs et al. | |
| 6,417,363 B1 | 7/2002 | Van Der Schaaf et al. | |
| 6,455,029 B1 * | 9/2002 | Angeletakis et al. | .......... 424/49 |
| 6,465,554 B1 | 10/2002 | Van Der Schaaf et al. | |
| 6,521,799 B2 | 2/2003 | Wagener et al. | |
| 6,525,125 B1 | 2/2003 | Giardello et al. | |
| 6,620,955 B1 | 9/2003 | Pederson et al. | |
| 6,649,146 B2 | 11/2003 | Angeletakis et al. | |
| 6,794,534 B2 | 9/2004 | Grubbs et al. | |
| 6,818,586 B2 | 11/2004 | Grubbs et al. | |
| 6,844,409 B2 | 1/2005 | Angeletakis et al. | |
| 6,861,386 B2 | 3/2005 | Angeletakis et al. | |
| 6,921,735 B2 | 7/2005 | Hoveyda et al. | |
| 7,001,590 B1 | 2/2006 | Angeletakis | |
| 7,060,769 B2 | 6/2006 | Angeletakis | |
| 7,060,770 B2 | 6/2006 | Angeletakis | |
| 2002/0153096 A1 | 10/2002 | Giardello et al. | |
| 2002/0185630 A1 | 12/2002 | Piccinelli et al. | |

FOREIGN PATENT DOCUMENTS

DE 19859191 A1 6/2000

(Continued)

OTHER PUBLICATIONS

International Organization for Standardization, Dental elastomeric impression materials; ISO 4823 (1992).

L. Lecamp et al., Polydimethyl siloxane photoreticulable par vole cationique-I, Eur. Polym. J., vol. 33, No. 9, 1453-1462 (1997).

Chevalier et al., Ring-opening olefin metathesis polymerisation (ROMP) as a potential cross-linking mechanism for siloxane polymers, J. of Inorganic and Organometallic Polymers, vol. 9, No. 3, 151-164 (1999).

Scholl et al., Synthesis and activity of a new generation of ruthenium-based olefin metathesis catalysts coordinated with 1,3-dimesityl-4,5-dihydroimidazol-2-ylidene ligands, Org. Lett., vol. 1, No. 6 953-956 (1999).

Kim et al., Surface-initiated ring-opening metathesis polymerization on Si/SiO2, Macromolecules 2000, 33(8), 2793-2795 (2000).

(Continued)

Primary Examiner—Ling-Siu Choi
(74) Attorney, Agent, or Firm—Wood, Herron & Evans, LLP

(57) ABSTRACT

A composition curable by a metathesis reaction upon mixing its components and comprising an olefin-containing substrate, a metathesis catalyst, and a reaction control agent for slowing the progress of the metathesis reaction. The metathesis catalyst is a ruthenium or osmium carbene complex catalyst having high activity and good air stability. In one embodiment, the catalyst is free of phosphine ligands. The reaction control agent is an organic compound that contains carbon-carbon double and/or triple bonds and one or more Group 14 atoms and is present in an amount effective to slow the progress of the metathesis reaction. In one embodiment, the olefin-containing substrate may comprise one or more oligomers or polymers having a >20 wt. % linear siloxane (Si—O—Si) backbone tethered and/or end-capped with functional olefin groups, such as cycloalkenyl group.

24 Claims, No Drawings

FOREIGN PATENT DOCUMENTS

| | | | |
|---|---|---|---|
| EP | 0796607 | A2 | 9/1997 |
| EP | 0771830 | A2 | 12/1999 |
| EP | 1025830 | A2 | 9/2000 |
| EP | 1241196 | A2 | 9/2002 |
| WO | 9839346 | A1 | 11/1998 |
| WO | 9900396 | A1 | 1/1999 |
| WO | 9900397 | A1 | 1/1999 |
| WO | 9929701 | A1 | 6/1999 |
| WO | 9950330 | A2 | 10/1999 |
| WO | 9960030 | A1 | 11/1999 |
| WO | 0046255 | A1 | 8/2000 |

\* cited by examiner

METATHESIS-CURABLE COMPOSITION WITH A REACTION CONTROL AGENT

CROSS REFERENCE TO RELATED APPLICATIONS

This application is a continuation-in-part of commonly-owned, U.S. patent application Ser. No. 10/891,918, now issued U.S. Pat. No. 7,173,097 issued Feb. 6, 2007 and entitled METATHESIS-CURABLE COMPOSITION WITH A REACTION CONTROL AGENT filed Jul. 15, 2004, which is a continuation-in-part of commonly-owned U.S. patent application Ser. No. 10/430,592 filed on May 6, 2003, now U.S. Pat. No. 7,060,770 issued Jun. 13, 2006 and entitled METATHESIS-CURABLE COMPOSITION WITH A REACTION CONTROL AGENT, and Ser. No. 10/430,953 filed on May 6, 2003, now U.S. Pat. No. 6,844,409 issued Jan. 18, 2005 and entitled COMPOSITION CURABLE BY METATHESIS REACTION, the disclosures of which are incorporated herein by reference in their entirety as if completely set forth herein below. Other commonly-owned related applications include: U.S. Pat. No. 6,455,029 issued Sep. 24, 2002 and entitled DENTAL IMPRESSION MATERIAL UTILIZING RUTHENTUM CATALYST; U.S. Pat. No. 6,649,146 issued Nov. 18, 2003 and entitled DENTAL IMPRESSION MATERIAL UTILIZING RUTHENIUM METATHESIS CATALYST; U.S. Pat. No. 6,861,386 issued Mar. 1, 2005 and entitled ACCELERATOR FOR METATHESIS CATALYST; and U.S. Pat. No. 7,060,769 issued Jun. 13, 2006 and entitled METHOD OF CURING A COMPOSITION BY METATHESIS REACTION USING REACTION CONTROL AGENT.

FIELD OF THE INVENTION

This invention relates to compositions that undergo a metathesis reaction initiated by a metathesis catalyst and that contain a reaction control agent for controlling the progress of the metathesis reaction. More specifically, the control agent slows the progress of the metathesis reaction, and depending on the nature of the control agent, may prevent completion of the reaction until the composition is exposed to temperatures higher than the mixing temperature.

BACKGROUND OF THE INVENTION

Addition polymerizable silicone resins are widely used in many fields such as electronics, health care and automotive applications. The polymerizable resins are cured as a two-part system using a hydrosilation reaction. A platinum catalyst is used in one part, the catalyst side, and a hydrogen terminated polydimethylsiloxane (HPDMS) in the other part, the base side, while both sides contain vinyl terminated polydimethylsiloxanes (PVDMS) resins. When these materials are cured at room temperature, they are referred to as room temperature vulcanized (RTV). The most common RTV materials are typically offered as a 10:1 ratio base/catalyst, such as RTV630 (GE Silicones), while some other RTV materials are offered at a 1:1 ratio, such as RTV6428 (GE Silicones). Various working times are required depending on the application from 2 minutes to several hours and may involve a heat curing step above ambient temperature. The working time is controlled with a retarder or inhibitor mixed with the catalyst component, such as an amine or acetylenic compound.

Another class of addition polymerizable silicone resins is the liquid silicone rubber (LSR) materials prepared through the liquid injection molding (LIM) process. The LSR materials are cured at a temperature of 120° C.-180° C. in a mold injected to after mixing. The mixture includes a retarder mixed with the catalyst component, such as an amine or acetylenic compound, which allows the hydrosilation reaction to occur at the mold temperature only.

Both the RTV and LSR types of formulations suffer from the shortcomings of the hydrosilation mechanism. These shortcomings include: (1) deactivation of the platinum catalyst by sulfur or other nucleophilic impurities; (2) high shrinkage, approximately 1%, due to the high reduction of free volume upon polymerization; (3) high cost of platinum metal needed for catalysis; (4) high cost of HPDMS and PVDMS resins; (5) requirement of two different resins to be employed, namely vinyl and hydrogen terminated; (6) undesirable hydrogen evolution from the decomposition of the hydrosiloxane cross-linkers that typically are present in these systems; and (7) vinyl functionalized PDMS resins have a low hydrocarbon content in the main chain after polymerization due to the presence of only an ethyl spacer, which may lead to a relatively high dielectric constant, which is an undesirable property for some electronic applications.

A new type of polymerization system has been recently developed that may potentially be used to replace addition-curable silicones and platinum catalysts in a wide variety of applications to thereby avoid the shortcomings of the hydrosilation mechanism discussed above. In this new metathesis reaction system, curing is achieved by a ring-opening metathesis polymerization (ROMP) mechanism. Metathesis is generally understood to mean the metal catalyzed redistribution of carbon-carbon double bonds. The polymerizable composition comprises a resin system that includes functionalities or groups that are curable by ROMP together with a metathesis catalyst, such as a ruthenium carbene complex. However, to efficiently utilize ROMP to prepare polymers, there is a need to control the progress of polymerization, particularly for molding applications.

In commonly-owned U.S. Pat. No. 6,649,146, a two-part room temperature ROMP-curable formulation containing siloxane polymers and fillers was described as usable as a dental impression material. The catalysts described therein are ruthenium carbene complexes containing phosphine ligands. These catalysts, however, are air sensitive because the phosphines can dissociate and oxidize, thereby leading to reduced shelf life. An alternative highly active ruthenium carbene complex that does not contain phosphine groups is described in Hoveyda et al. U.S. Pat. No. 6,921,735. This alternative catalyst has a good air stability profile. However, when this alternative catalyst is substituted for the catalysts containing the phosphine ligands, the composition exhibits a very short working time after mixing, on the order of 20 seconds, which makes the use of these compositions impractical in many applications, such as dental impression materials. There is thus a need to provide a room temperature ROMP-curable formulation that has good air stability as well as a longer working time after mixing.

In addition to ROMP, other metathesis reaction systems utilize metathesis catalysts, for example ring closing metathesis, acyclic diene metathesis polymerization, ring opening metathesis and cross metathesis. There is further a need for controlling the progress of reaction in these other metathesis reaction systems.

SUMMARY OF THE INVENTION

The present invention provides a composition that upon mixing of its components undergoes a metathesis reaction, wherein the composition contains components for controlling and catalyzing the metathesis reaction. The composition comprises a ruthenium or osmium carbene complex catalyst that is capable of initiating a metathesis reaction, such as ring-opening metathesis polymerization (ROMP), a reaction control agent for slowing the progress of the reaction, and a metathesis-curable olefinic substrate. The catalyst may have the following structure:

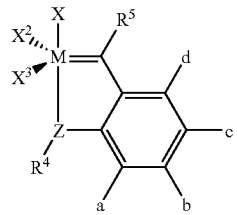

wherein:

M is ruthenium or osmium,

X is an alkylidene ligand with basicity higher than that of tricyclohexylphosphine ($PCy_3$), $X^2$ and $X^3$ are either the same or different and are any anionic ligand, Z is oxygen (O) or sulfur (S), and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

The composition further comprises a reaction control agent, which slows the progress of the metathesis reaction. The control agent allows the composition to be cured after a certain delayed time after mixing (work time or pot life) or allows for completion of curing only by heating to temperatures above the mixing temperature at any time during the work time period. The control agent, and the amount thereof, also allows for control of the viscosity build up rate as the metathesis reaction proceeds, which is useful for many molding applications. The reaction control agent is an organic compound that contains carbon-carbon double and/or triple bonds and one or more central Group 14 atoms, and can further contain, in the case of a Si central atom, oxygen atoms connected to the silicon to form siloxane bonds. More particularly, the reaction control agent has the following structure:

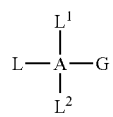

wherein:

G is selected from the group consisting of: $L^3$,

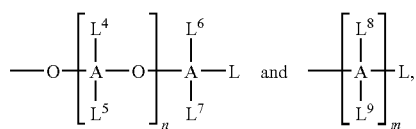

L is a hydrocarbon fragment containing a double or triple bond, $L^1$-$L^9$ are each independently selected from the group consisting of L, alkyl, aryl, aralkyl or haloalkyl, A is a Group 14 atom, n=0-20, and m=0-20.

Advantageously, L is an allyl (2-propenyl), vinyl (ethenyl), ethynyl, or propargyl (2-propynyl) group. Also advantageously, the reaction control agent includes more than one L group. In an exemplary embodiment of the invention, the reaction control agent is tetraallyl silane (TAS):

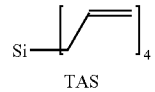

TAS

In another exemplary embodiment, the reaction control agent is tetraallyloxy silane (TAOS).

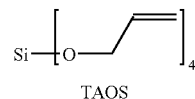

TAOS

The catalyst and the reaction control agent are combined with an olefinic substrate to provide a composition that undergoes the metathesis reaction with a controlled rate. In one embodiment of the present invention, thermal or photochemical activation, for example, is needed to complete the metathesis reaction. In another embodiment, the composition comprises any cycloalkenyl-functionalized oligomer or polymer that can undergo polymerization via ROMP. In another embodiment of the present invention, the composition comprises an olefin-containing resin system comprising one or more oligomers or polymers having a >20 wt. % linear siloxane (Si—O—Si) backbone that can be tethered and/or end-capped with functional olefin groups, such as cycloalkenyl groups, that can undergo a metathesis reaction. In yet another embodiment, norbornenylethyl terminated and/or tethered polydimethylsiloxane resins are used. In yet another embodiment, cycloolefins such as dicyclopentadiene (DCPD) can be used.

DETAILED DESCRIPTION

The present invention provides formulations of ruthenium or osmium carbene complexes together with reaction control agents that allow control of the progress of a metathesis reaction on an olefin-containing substrate.

The catalysts useful in the present invention include ruthenium or osmium carbene complexes having the following structure:

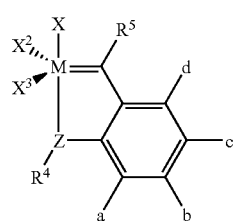

wherein:

M is ruthenium or osmium,

X is an alkylidene ligand with basicity higher than that of tricyclohexylphosphine ($PCy_3$), $X^2$ and $X^3$ are either the same or different and are any anionic ligand, Z is oxygen (O) or sulfur (S), and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S.

In one embodiment, the ring-opening metathesis activity and air stability of the catalyst can be increased by using an alkylidene ligand X, such as a saturated imidazolidine ligand, having a basicity or proton affinity higher than that of tricyclohexylphosphine ($PCy_3$) ligands. The ligands X may be 4,5-dihydroimidazol-2-ylidenes, which have the following general structure:

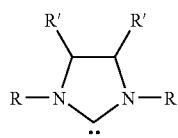

R may be mesityl (2,4,6 trimethylphenyl) and R' may be H or phenyl. These substituted alkylidene ligands X have a basicity or proton affinity higher than that of tricyclohexylphosphine, which is believed to contribute to the higher activity and higher air stability. By way of further example, X may be the 1,3-bis(2,4,6-trimethylphenyl)-imidazol-2-ylidene (sIMES) ligand as shown here:

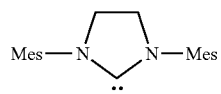

wherein Mes is mesityl (2,4,6 trimethylphenyl). Other 4,5-dihydroimidazol-2-ylidenes can also be used to afford ruthenium carbene complexes, such as the following ligands:

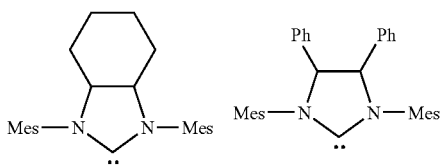

wherein Mes is mesityl, and Ph is phenyl. In an exemplary embodiment, the catalyst is free of phosphine ligands.

In another exemplary embodiment, the catalyst has the structure above in which M is ruthenium, X is an alkylidene ligand with basicity higher than that of tricyclohexylphosphine ($PCy_3$), $X^2$ and $X^3$ are halogen atoms, Z is oxygen, $R^4$ is a $C_1$ to $C_{10}$ alkyl fragment, a, b, c, and d are each either hydrogen or a $C_1$ to $C_{10}$ alkyl or a $C_1$ to $C_{10}$ alkoxy group, and $R^5$ is hydrogen.

In yet another exemplary embodiment, the catalyst has the structure above in which M is ruthenium, X is 1,3-bis(2,4,6-trimethylphenyl)-imidazol-2-ylidene (sIMES), $X^2$ and $X^3$ are chlorine atoms, Z is oxygen, $R^4$ is either isopropyl, ethyl or methyl, a, b, c, and d are each either hydrogen, ethoxy or methoxy, and $R^5$ is hydrogen. An example of this type of exemplary catalyst (Catalyst A) is 1,3-bis-(2,4,6-trimethylphenyl)-2-(imidazolidinylidene) dichloro(o-isopropoxyphenylmethylene) ruthenium having the following structure:

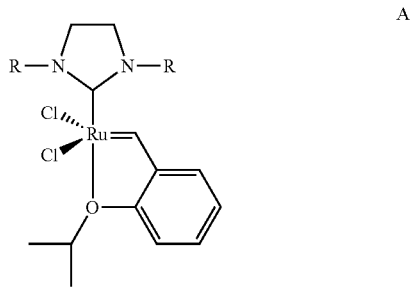

wherein R is mesityl ($R^4$=isopropyl and a, b, c, and d are each H). Another example, Catalyst B, is similar to Catalyst A except that $R^4$ is methyl and c is methoxy ($CH_3O$). Yet another example, Catalyst C, is similar to Catalyst A except that $R^4$ is ethyl and c is ethoxy ($CH_3CH_2O$). Other examples for this category of catalysts, as well as the synthesis of these catalysts, are fully described in U.S. Pat. No. 921,735 issued Jul. 26, 2005 and incorporated by reference herein in its entirety.

The composition further comprises at least one reaction control agent. After mixing of the composition components, the control agent slows the metathesis reaction, and thereby allows for an increase in the time period before cure, or before the metathesis reaction proceeds to completion or to a desired extent short of completion. The length of this time period, also called work time or pot life, may be controlled by preventing completion of the reaction until the composition is heated to a temperature above the mixing temperature, for example about 30° C. or more above the mixing temperature. Alternatively, the work time may be controlled by exposure to light. The reaction control agent also allows for control of the viscosity build up as the metathesis reaction proceeds, which is useful for many molding applications. The reaction control agent is an organic compound that contains carbon-carbon double and/or triple bonds and one or more central Group 14 atoms, and can further contain, in the case of silicon as the central atom(s), oxygen atoms connected to silicon to form siloxane bonds. The reaction control agent has the structure shown below:

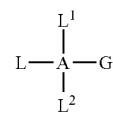

wherein:

G is selected from the group consisting of: $L^3$,

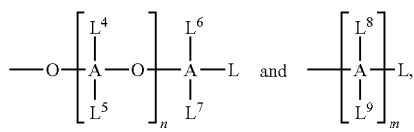

L is a hydrocarbon fragment containing a double or triple bond;

$L^1$-$L^9$ are each independently selected from the group consisting of L, alkyl, aryl, aralkyl or haloalkyl;

A is a Group 14 atom;

n=0-20; and m=0-20.

Of the Group 14 atoms, which include C, Si, Ge, Sn and Pb, the central atom is advantageously Si, Ge or Sn, and more advantageously Si.

In one embodiment of the present invention, G=$L_3$ such that the reaction control agent is a tetracoordinated compound having at least one substituent group L that is a hydrocarbon fragment containing a double or triple bond. Allyl and vinyl groups are hydrocarbon fragments containing a double bond, for example, and alkynyl groups, such as propargyl and ethynyl groups, are hydrocarbon fragments containing a triple bond, for example. For the other substituent groups $L^1$, $L^2$, $L^3$, if not a hydrocarbon fragment containing a double or triple bond, then the substituent group is an alkyl, aryl, aralkyl or haloalkyl group, which are essentially inert to the metathesis reaction. Thus, it is the hydrocarbon fragment containing the double or triple bond that determines the extent of the retardation of the metathesis reaction, such that a greater number of such hydrocarbon fragments would be expected to achieve longer working times than similar structures containing fewer of such hydrocarbon fragments. An exemplary inert substituent is the methyl group.

In the embodiment of the present invention where G is defined as:

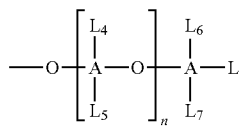

the central atom A is Si, such that the reaction control agent contains a straight chain siloxane compound in which the ends of the chain are capped by hydrocarbon fragments containing a double or triple bond. The substituent groups within the chain (i.e., $L^1$, $L^2$, $L^4$, $L^5$, $L^6$, $L^7$) may also be hydrocarbon fragments containing double or triple bonds or may be an inert substituent including alkyl, aryl, aralkyl or haloalkyl groups. By way of example, where A is silicon and n=0, a disiloxane compound is formed, such as divinyltetramethyldisiloxane.

In the embodiment of the present invention where G is:

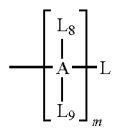

a structure is formed having a chain of single-bonded Group 14 atoms where the ends of the chain are capped by hydrocarbon fragments containing a double or triple bond. As with the previous embodiment, the substituent groups within the chain (i.e., $L^1$, $L^2$, $L^8$, $L^9$) may be either the hydrocarbon fragment with the double or triple bond or may be an inert alkyl, aryl, aralkyl or haloalkyl group. Where m=2, for example, a 3 atom chain is formed with 2 hydrocarbon fragment double or triple bond end groups and 6 $L^1$-$L^9$ substituent groups.

Combinations of two or more reaction control agents are contemplated by the present invention. For example, a mixture of agents may be used, each affording different viscosity build-up characteristics. By way of further example, one reaction control agent may be used that slows or prevents curing of the composition in the absence of heat, while a second reaction control agent is used that slows or prevents curing in the absence of light.

The composition further comprises an olefin-containing substrate (compound or mixture of compounds), such as a cyclic olefin-containing compound or mixture of compounds or an acyclic olefin-containing compound or mixture of compounds, which undergoes a metathesis reaction, such as ROMP, when mixed with the ruthenium carbene complex. The progression of the reaction is controlled by the at least one reaction control agent, such as tetraallyl silane (TAS) or tetraallyloxysilane (TAOS), to increase the working time of the composition and to control the viscosity build up. In one exemplary embodiment of a composition curable by ROMP, the resin system comprises at least one cyclic olefin functionalized >20 wt. % linear siloxane (Si—O—Si) backbone oligomer or polymer that is telechelic, tethered, tri-functional and/or quadri-functional. More specifically, the compound or mixture of compounds curable by ROMP may comprise one or a combination of the following: a polymerizable telechelic siloxane-based polymer end-capped with an olefin group curable by ROMP; a polymerizable siloxane-based polymer tethered and end-capped with an olefin group curable by ROMP; a polymerizable tri-functional siloxane-based oligomer or polymer end-capped with an olefin group curable by ROMP; and a polymerizable quadri-functional siloxane-based oligomer or polymer end-capped with an olefin group curable by ROMP. The olefin groups may be cycloalkenyl groups, for example norbornenyl or norbornenylethyl groups.

By way of example and not limitation, one category of oligomers and/or polymers that may be used in compositions of the present invention include telechelic (end-functionalized/end-capped) polymers with any of a variety of backbones comprising a >20 wt. % linear siloxane as long as the chain ends are functionalized with reactive olefin groups, such as cycloalkenyl groups. For example, the resin may be a telechelic PDMS terminated with NBE groups according the following structure:

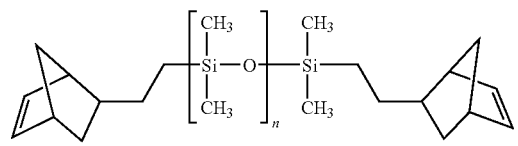

where n=5-5000, for example 27-1590. Other examples of telechelic polysiloxanes are those having the following structure:

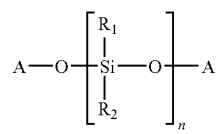

where n=5-5000, such as 27-1590;

$R_1$, $R_2$=$C_1$-$C_{18}$ hydrocarbon or

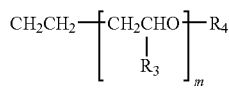

where $R_3$, $R_4$=H or $C_1$-$C_{18}$ hydrocarbon, and m=1-10; and

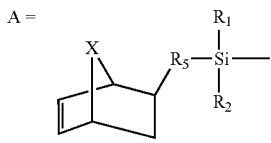

X=$CH_2$, S, O
$R_5$=$C_0$-$C_{18}$ hydrocarbon
$R_6$=$C_0$-$C_{18}$ hydrocarbon

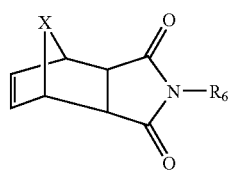

Another category of oligomers and/or polymers that may be used in compositions of the present invention include oligomers or polymers comprising a >20 wt. % linear siloxane backbone tethered and end-capped with groups curable by a metathesis reaction, such as cycloalkenyl groups. The oligomers or polymers may have any of a variety of siloxane-based backbones, particularly PDMS, with pendant groups incorporated within the backbone or main chain that protrude therefrom thus forming the tethered structure. As with the telechelic polymers, the chain ends are functionalized or capped with reactive olefin groups, such as cycloalkenyl groups, for example norbornenyl or norbornenylethyl groups. The pendant groups may also be cycloalkenyl groups, such as norbornenyl or norbornenylethyl groups. For example, the resin may be a PDMS tethered and end-capped with NBE groups according the following structure:

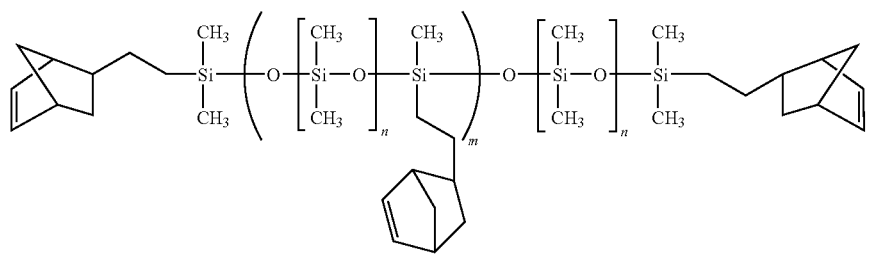

where n=5-5000, for example 27-1590, and m=1-100, for example 1-10. In an exemplary embodiment of the present invention, the resin system includes at least one PDMS tethered and end-capped with NBE groups.

Yet another category of oligomers and/or polymers that may be used in compositions of the present invention include tri- or quadri-functional oligomers or polymers having a >20 wt. % linear siloxane backbone end-functionalized or end-capped with an olefin group curable by a metathesis reaction, such as cycloalkenyl groups, for example norbornenyl or norbornenylethyl groups. An example of such polymer is quadri-functional PDMS, end-capped with NBE groups.

By way of further example, the resin system may comprise both the telechelic oligomer or polymer and the tethered oligomer or polymer, each functionalized with groups curable by ROMP, or may comprise the telechelic oligomer or polymer and the tethered oligomer or polymer and the quadri-functional oligomer or polymer, each functionalized with groups curable by ROMP. Thus, the resin formulation may be varied to obtain desired physical properties in the uncured and cured material.

The cycloalkenyl functionalized PDMS resins that are cured via ROMP have a higher hydrocarbon content than the vinyl functionalized PDMS resins that are used in hydrosilation reactions. The higher hydrocarbon content may lead to a lower dielectric constant, which is desirable for many electronic applications.

In addition to the above category of oligomers and polymers, the olefin-containing substrate may comprise any other cycloalkenyl-functionalized oligomers or polymers that may undergo polymerization via ROMP mechanism, such as reactive cycloolefins, for example DCPD. Acyclic olefin-functionalized compounds that may undergo acyclic diene metathesis polymerization are also contemplated.

In another embodiment of the present invention, the olefin-containing substrate may comprise a base resin as set forth in commonly-owned, co-pending U.S. patent application Ser. Nos. 11/276,270 and 11/276,273, each filed on Feb. 21, 2006, the disclosures of which are incorporated herein by reference in their entirety as if completely set forth herein below.

The composition of the present invention contemplates a catalyst paste and base paste that upon mixture with one another, form a curable paste/paste system in which the metathesis reaction proceeds. Generally, in this system, the catalyst paste comprises the metathesis catalyst for initiating polymerization, and a solvent for the catalyst that is miscible or dispersible with the base paste and that does not interfere with the metathesis reaction. The solvent may be, for example, 3-phenyl-heptamethyl-trisiloxane or an alkyl methylsiloxane-arylalkylmethylsiloxane copolymer such as a 45-55% hexylmethylsiloxane/45-55% 2-phenylpropylmethylsiloxane copolymer with a viscosity of 1250 csk. Another exemplary solvent is a phenyl trimethicone such as SilCare® 15M40 (Clariant GmbH, Sulzbach, Germany). Yet another exemplary solvent is a partially phenyl substituted poly(dimethylsiloxane), such as Dow Corning Fluid 556. The base paste generally comprises the olefin-containing substrate that is curable via ROMP or other metathesis reaction, and the reaction control agent. The composition may further include filler systems and/or optional additives suitable for the particular application, such as pigments or surfactants, that do not interfere with the reaction. The composition may also include additional curing agents, such as photointiators and photocoinitiators, to provide an additional curing mechanism besides the metathesis catalyst.

The compositions of the present invention may be used to replace hydrosilation reaction systems using platinum catalysts and dual resin systems. The metathesis reaction is a homo-reaction using a single resin system, which simplifies the formulation, for example using the NBE-functionalized PDMS resins in combination with a ruthenium carbene complex catalyst. The compositions of the present invention provide two-part cured elastomers that function well as dental impression materials, for example. The compositions of the present invention have good air stability as well as high catalyst activity so as to provide the longer storage time in air that is desired by dental professionals. These benefits are achieved using a catalyst with low sulfur sensitivity compared to platinum hydrosilation catalysts, which is a further advantage when these compositions are used in the oral cavity as impression materials where latex gloves containing sulfur impurities and other medicaments have previously been known to deactivate catalysts.

The reaction control agent is incorporated into the base paste, to slow the ROMP rate upon mixing of the catalyst paste and base, thereby increasing the working time of the resin before cure, and even to prevent completion of the ROMP in the absence of an elevated temperature above the mixing temperature or in the absence of exposure to light. The presence of the reaction control agent provides a working time after mixing that is in a usable range for dental impression materials. While numerous retarders are known for use with the platinum catalysts in the hydrosilation mechanism, unexpectedly, some of the most common of them are not effective with the ruthenium carbene catalysts in the ROMP mechanism. However, tetraallyl silane (TAS), for example, has been found to provide significantly increased working time. Similarly, other compounds having a Group 14 central atom and one or more ligands having a hydrocarbon fragment and carbon-carbon double or triple bond are also expected to be effective.

EXAMPLES

Various resins were formulated and tested and their properties compared to that of two commercial dental impression materials. While the commercial products are mixed with a 1:1 base/catalyst ratio, the resins of the present invention were mixed with a 4:1 ratio. It may be understood that other ratios may be used. A telechelic polydimethylsiloxane (PDMS) end-capped with norbornenylethyl groups was used in the base paste, with n=243 as shown below:

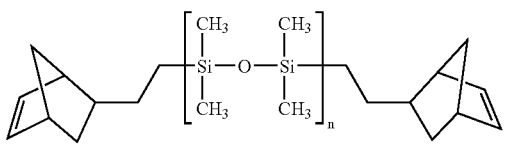

The reaction control agent used was tetraallyl silane (TAS). The base paste formulation is provided below in Table 1:

TABLE 1

| Base Paste Composition (wt. %) | |
| --- | --- |
| PDMS resin end-capped with norbornenylethyl groups (n = 243) | 60.95 − x |
| Reaction Control Agent | x |
| Calcium Silicate Wollastonite (2-10 μm) | 20.5 |
| Sub-micron Silica | 18.0 |
| Surfactant | 0.50 |
| Pigment | 0.05 |
| Total | 100 |

Three catalysts, Catalysts A, B, and C, of the following formula were used in the catalyst paste, each obtained from Materia, Inc., Pasadena, Calif., under Product Nos. C627, C629 and C657, respectively:

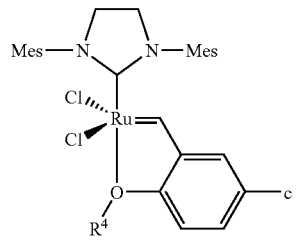

As described above, for Catalyst A, $R^4$ is isopropyl and c is H; for Catalyst B, $R^4$ is methyl and c is methoxy; and for Catalyst C, $R^4$ is ethyl and c is ethoxy. The catalyst component was formulated by dissolving it in a partially phenyl substituted polymethylsiloxane, in particular, Dow Corning Fluid 556, followed by compounding with fillers. The catalyst paste formulation is provided in Table 2:

TABLE 2

| Catalyst Paste Composition (wt. %) | |
| --- | --- |
| Dow Corning Fluid 556 | 39.955 |
| Calcium Silicate Wollastonite (2-10 μm) | 45 |
| Sub-micron Silica | 15 |
| Catalyst | 0.045 |
| Total | 100 |

The base paste and catalyst paste were mixed at ambient temperature. The physical properties of dental impression materials prepared with the above base pastes and catalyst pastes and the two commercial compositions are provided in Table 3. The numbers in parentheses indicate standard deviation.

The desired work time (WT) and set time (ST) ranges for dental impression materials are 90-140 sec for WT and less than 300 sec for ST. The work times detailed in Table 3 show that different TAS levels for each type of catalyst may be necessary to produce the desired WT and ST ranges. The physical properties of the resins of the present invention were similar to the commercial compositions, and these properties can be further altered by altering the type of filler and the extent of filler loading.

After Test Resin 1 was allowed to cure at room temperature, the composition was further subjected to post-curing for 1 hour at 175° C. to ascertain the affect of subsequent post-curing on the physical properties of the compositions of the present invention. The post-cure had the benefit of significantly increasing the tensile strength to 3.75 (0.14) MPa and the tear strength to 7.6 (0.2) N/mm. The decrease in elongation to 222 (19) % and the increase in hardness to 58 (1) were relatively small.

Table 4 provides the WT and ST for each catalyst controlled with the same TAS content, as well as with no addition of the TAS reaction control agent. Without the addition of a reaction control agent, the compositions quickly proceed toward a complete cure and exhibit a WT far below the practical level necessary for use as a dental impression material. With 1500 ppm of a TAS reaction control agent, the metathesis reaction by Catalyst A was controlled to the desired WT and ST ranges for a dental impression material. For the metathesis reactions by Catalysts B and C, the reaction was slowed significantly by the 1500 ppm level of TAS compared to no TAS addition. However, for practical purposes, when used as a dental impression material, a lower TAS content should be used such that the WT and ST are not longer than desired.

obtained from Materia, Inc. under Product No. C848. The base and catalyst pastes were prepared as described above. Prior to mixing the pastes together, paste samples for preparing each resin type were stored in an oven at an elevated temperature above ambient temperature, namely 61° C., for 4 days, 8 days, or 15 days. For comparison, paste samples were also mixed together at ambient temperature without storing at elevated temperature. The WT and ST were then measured for each composition.

TABLE 5

| | Test Resin 9 | Comparative Resin 10 |
|---|---|---|
| Mixing Ratio | 4:1 | 4:1 |
| Catalyst (ppm, resin basis) | 224 | 448 |
| TAS (ppm, resin basis) | 1290 | 0 |
| Manual Work/Set Time (sec) 25° C. Initial | 90/165 | 153/435 |
| Manual Work/Set Time (sec) 61° C., 4 days | 136/296 | 74/261 |

TABLE 3

| | Take 1 Tray (Kerr) | Imprint II Garant HB Heavy Body (3M ESPE) | Test Resin 1 | Test Resin 2 | Test Resin 3 |
|---|---|---|---|---|---|
| Catalyst | Pt-based | Pt-based | A | B | C |
| Mixing Ratio | 1:1 | 1:1 | 4:1 | 4:1 | 4:1 |
| TAS (ppm, resin basis) | N/A | N/A | 1500 | 250 | 100 |
| Consistency (mm) | 28 (1) | 31 (1) | 31 (1) | 32 (1) | 32 (1) |
| Manual Work Time WT (sec) | 118 | 185 | 90 | 92 | 104 |
| Set Time ST (sec) | 242 | 341 | 174 | 233 | 265 |
| Tensile Strength (MPa, Die D) | 3.0 (0.7) | 3.2 (0.2) | 2.41 (0.12) | 2.07 (0.27) | 1.95 (0.20) |
| Elongation (%, Die D) | 234 (73) | 98.1 (9.6) | 229 (16) | 166 (22) | 136 (24) |
| Hardness, Shore A (Room T) | 52 (1) | 54 (1) | 54 (1) | 51 (1) | 54 (1) |
| Tear Strength (N/mm) | 6.8 (0.2) | 4.4 (0.3) | 5.1 (0.1) | 3.6 (0.3) | 4.1 (0.1) |

TABLE 4

| | Test Resin 1 | Test Resin 4 | Test Resin 5 | Comparative Resin 6 | Comparative Resin 7 | Comparative Resin 8 |
|---|---|---|---|---|---|---|
| Mixing Ratio | 4:1 | 4:1 | 4:1 | 4:1 | 4:1 | 4:1 |
| Catalyst (224 ppm, resin basis) | A | B | C | A | B | C |
| TAS (ppm, resin basis) | 1500 | 1500 | 1500 | 0 | 0 | 0 |
| Manual Work Time (sec) | 90 | 153 | 235 | 8 | 11 | 12 |
| Set Time (sec) | 174 | 435 | 550 | 24 | 30 | 42 |

Table 5 shows the effect of exposure to elevated temperatures during storage on a composition of the present invention compared to a composition using a catalyst containing a phosphine ligand. Test Resin 9 of the present invention utilized Catalyst A in the catalyst paste. Comparative Resin 10 used a catalyst having the following structure:

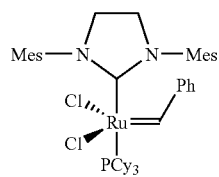

TABLE 5-continued

| | Test Resin 9 | Comparative Resin 10 |
|---|---|---|
| Manual Work/Set Time (sec) 61° C., 8 days | 128/282 | No Cure |
| Manual Work/Set Time (sec) 61° C., 15 days | 184/430 | No Cure |

The catalyst used in Resin 10 is far more sluggish at room temperature than Catalyst A used in Test Resin 9, which is expected, since Catalyst A is designed to have higher activity as a metathesis catalyst. Catalyst A is also more stable than the other catalyst, which can be attributed to the presence of the phosphine ligand ($PCy_3$) in the other catalyst. Phosphines easily oxidize in the presence of atmospheric oxygen to give the corresponding phosphine oxide, which cannot function as a ligand for the ruthenium carbene complex. The result is oxidative degradation of the catalyst complex, and ultimately, the inability of the catalyst to cure the composition. Test Resin 9 is capable of being stored longer without degradation and deactivation of the catalyst. Thus, in an exemplary embodiment of the present invention, the catalyst is phosphine-free.

By using a reaction control agent in the formulation in combination with a high activity catalyst free of phosphines, it is believed that desired work times and set times can be achieved at room temperature, and the catalyst paste may be stored for a longer period before the catalyst loses its ability to cure the composition. Also, some reaction control agents may be effective to prevent the metathesis reaction from either being initiated or from being completed absent application of an elevated temperature greater than the mixing temperature or exposure to light within a certain time window. In these embodiments, the metathesis reaction should be completed by heat or light curing before the catalyst loses its potency to metathesize the olefinic compound, i.e., before the catalyst deactivates.

The compositions of the present invention are particularly contemplated for use as dental impression materials. However, the invention is not so limited. Other potential uses for compositions of the present invention include automotive applications, electric/electronics applications and flexible adhesives therefor, electro and appliances, medical applications, textile applications, and other miscellaneous applications. By way of example and not limitation, automotive applications may include: distributor caps, cable bushings, loudspeaker covers, housing seals, bellows, plug seals, spark plug boots, vent flaps, grommets for weather packs, central door locker membranes, o-rings, gaskets, bushings, boots, and combined elements with thermoplastics. By way of example and not limitation, electric/electronics applications may include: sockets for antennas, terminals, plug connections, conductors (overvoltage), insulators (high voltage), housing seals, reinforced insulating hoses, vibration dampers (collectors), switch membrane covers (damp room switches), watch seals, insulating parts for hot adhesive guns, key pads for computers and telephones, anode caps, insulators and surge arresters, diaphragms, grommets, cable seals, and covers for switches. By way of example and not limitation, electro and appliance applications may include: small seals, cable bushings, reinforced insulating hoses, lamp seals, appliance feet, membranes, o-rings, diffuser for hair dryers, gaskets for faucets, gaskets for pressure cookers, detergent seals for dish washers, parts for coffee and espresso machines, coated glass fiber hoses for electric stoves, and water diffuser for shower bath. By way of example and not limitation, medical applications may include: seals for medical appliances, syringe plungers, breast nipple protectors, base plates (dental), inflating bellows, catheters, instrument mats, sterilization mats, O-rings for dialysers, earplugs, pipette nipples, catheter holders, cannula protection sleeves, nose clamps, valves and bellows for respirators, baby bottle nipples, baby pacifiers, stoppers, respiratory masks, Foley catheters, electrodes, cements used in orthopedic surgery such as for bone cementation and vertebroplasty procedures, parts for dental applications, and parts for medical equipment. By way of example and not limitation, textile applications may include: textile coating for conveyor belts, tents, compensators and technical applications, sleeves for electrical and heat insulation, heat reflecting fabrics for steel worker's coats, airbag coating, and printing inks. By way of example and not limitation, miscellaneous applications may include: swimming goggles, snorkels and mouthpieces for snorkels, elements for sport shoes, diving masks, swimming caps, respiratory devices, photocopier rolls and butcher's gloves. All of the foregoing are intended to be exemplary uses for the compositions of the present invention and are not intended to limit the invention in any way.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative method and illustrative examples shown and described. Accordingly, departures may be made from such details without departing from the scope or spirit of the general inventive concept.

What is claimed is:

1. A composition capable of undergoing a metathesis reaction upon mixing its components, the components comprising:

an olefin-containing substrate capable of undergoing a metathesis reaction;

a carbene complex catalyst capable of initiating the metathesis reaction in the composition, wherein the catalyst has the structure:

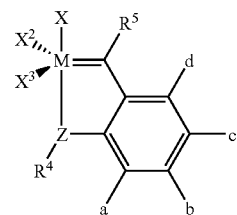

wherein:

M is ruthenium or osmium,

X is an alkylidene ligand with basicity higher than that of tricyclohexylphosphine ($PCy_3$), Z is oxygen (O) or sulfur (S)

$X^2$ and $X^3$ are either the same or different and are any anionic ligand, and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S; and at least one reaction control agent for slowing the progress of the metathesis reaction after mixing the composition components and having the structure:

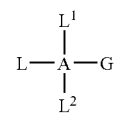

wherein:

G is selected from the group consisting of: $L^3$,

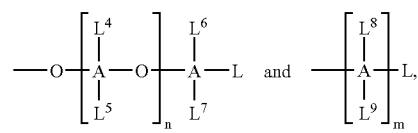

L is a hydrocarbon fragment containing a double or triple bond, $L^1$-$L^9$ are each independently selected from the group consisting of L, alkyl, aryl, aralkyl or haloalkyl, A is a Group 14 atom, n=0-20, and m=0-20.

2. The composition of claim 1 wherein M is ruthenium; X is 1,3-bis(2,4,6-trimethylphenyl)-imidazol-2-ylidene; $X^2$ and $X^3$ are chlorine atoms; Z is oxygen; $R^4$ is isopropyl, ethyl or methyl; a, b, c, and d are each either hydrogen, ethoxy or methoxy; and $R^5$ is hydrogen.

3. The composition of claim 1 wherein the X has the structure:

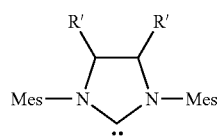

wherein Mes is mesityl and R' is hydrogen or phenyl.

4. The composition of claim 1 wherein the X has the structure:

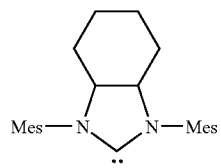

wherein Mes is mesityl.

5. The composition of claim 1 wherein the catalyst is free of phosphines.

6. The composition of claim 1 wherein L is a hydrocarbon fragment containing an allyl group, a vinyl group, an ethynyl group or a propargyl group.

7. The composition of claim 1 wherein A is silicon.

8. The composition of claim 1 wherein the at least one reaction control agent includes tetraallyl silane or tetraallyloxysilane.

9. The composition of claim 1 wherein the olefin-containing substrate includes at least one oligomer or polymer having a >20 wt. % linear siloxane (Si—O—Si) backbone functionalized with cycloalkenyl groups capable of undergoing a metathesis reaction.

10. A composition capable of undergoing a metathesis reaction upon mixing of its components, the components comprising:

an olefin-containing substrate comprising at least one oligomer or polymer having a >20 wt. % linear siloxane (Si—O—Si) backbone functionalized with olefin groups capable of undergoing a metathesis reaction, wherein the at least one oligomer or polymer is selected from the group consisting of: a telechelic oligomer or polymer end-capped with the olefin groups, an oligomer or polymer tethered and end-capped with the olefin groups, a tri-functional oligomer or polymer end-capped with the olefin groups, and a quadri-functional oligomer or polymer end-capped with the olefin groups;

a ruthenium carbene complex catalyst capable of initiating the metathesis reaction in the composition, wherein the catalyst has the formula:

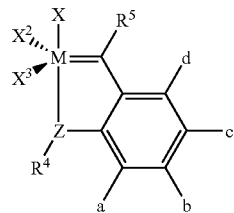

wherein:

M is ruthenium or osmium,

X is an alkylidene ligand with basicity higher than that of tricyclohexylphosphine ($PCy_3$), Z is oxygen (O) or sulfur (S)

$X^2$ and $X^3$ are either the same or different and are any anionic ligand, and $R^4$, $R^5$, a, b, c, and d are the same or different and are each a linear, branched, cyclic or polycyclic organic residue optionally containing siloxane groups (Si—O—Si) and optionally containing heteroatoms selected from the group consisting of B, N, O, Si, P, and S; and at least one reaction control agent for slowing the progress of the metathesis reaction after mixing the composition components and having the structure:

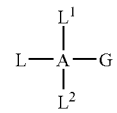

wherein:

G is selected from the group consisting of: $L^3$,

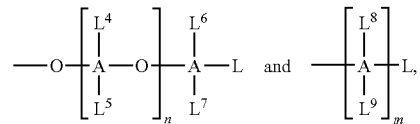

L is a hydrocarbon fragment containing an allyl group, a vinyl group, an ethynyl group or a propargyl group, $L^1$-$L^9$ are each independently selected from the group consisting of L, alkyl, aryl, aralkyl or haloalkyl, A is a Group 14 atom, n=0-20, and m=0-20.

11. The composition of claim 10 wherein the olefin groups are norbornenyl groups or norbornenylethyl groups.

12. The composition of claim 10 wherein the olefin-containing substrate includes polydimethylsiloxane tethered and end-capped with norbornenylethyl groups and having the formula:

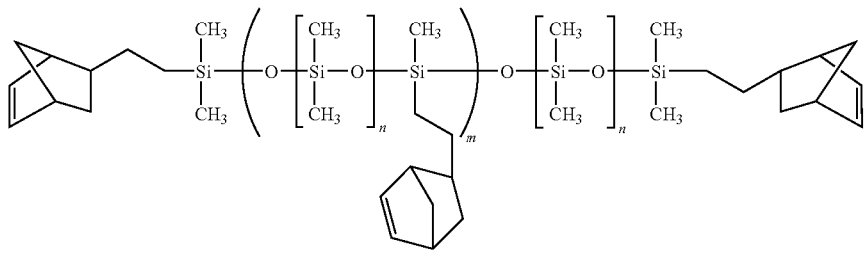

where n=5-5000, and m=1-100.

13. The composition of claim 10 wherein the olefin-containing substrate includes telechelic polydimethylsiloxane end-functionalized with norbornenylethyl groups and having the formula:

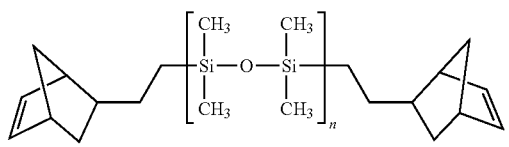

wherein n=5-5000.

14. The composition of claim 10 wherein M is ruthenium; X is 1,3-bis(2,4,6-trimethylphenyl)-imidazol-2-ylidene; $X^2$ and $X^3$ are chlorine atoms; Z is oxygen; $R^4$ is isopropyl, ethyl or methyl; a, b, c and d are each either hydrogen, ethoxy or methoxy; and $R^5$ is hydrogen.

15. The composition of claim 10 wherein the X has the structure:

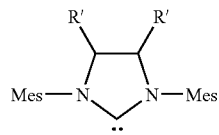

wherein Mes is mesityl and R' is hydrogen or phenyl.

16. The composition of claim 10 wherein the X has the structure:

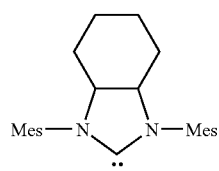

wherein Mes is mesityl.

17. The composition of claim 10 wherein the catalyst is free of phosphines.

18. The composition of claim 10 wherein L is a hydrocarbon fragment containing an allyl group, a vinyl group, an ethynyl group or a propargyl group.

19. The composition of claim 10 wherein A is silicon.

20. The composition of claim 10 wherein the at least one reaction control agent includes tetraallyl silane or tetraallyloxysilane.

21. A curable composition comprising:
an olefin-containing substrate comprising at least one oligomer or polymer having a >20 wt. % linear siloxane (Si—O—Si) backbone functionalized with cycloalkenyl groups capable of undergoing a metathesis reaction;
a ruthenium carbene complex catalyst capable of initiating the metathesis reaction in the composition, wherein the catalyst has the structure:

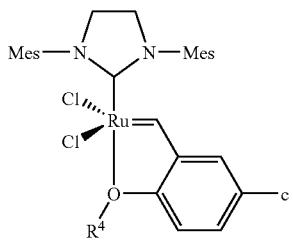

wherein $R^4$ is isopropyl, ethyl or methyl, and c is hydrogen, methoxy or ethoxy; and
a reaction control agent for slowing the progress of the metathesis reaction, wherein the reaction control agent is tetraallyl silane or tetraallyloxysilane.

22. The composition of claim 21 wherein the cycloalkenyl groups are norbornenyl groups or norbornenylethyl groups.

23. The composition of claim 21 wherein the olefin-containing substrate includes polydimethylsiloxane tethered and end-capped with norbornenylethyl groups and having the formula:

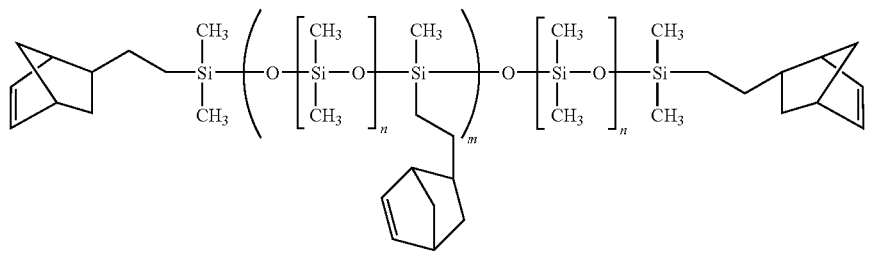

where n=5-5000, and m=1-100.

24. The composition of claim 21 wherein the olefin-containing substrate includes telechelic polydimethylsiloxane end-functionalized with norbornenylethyl groups and having the formula:
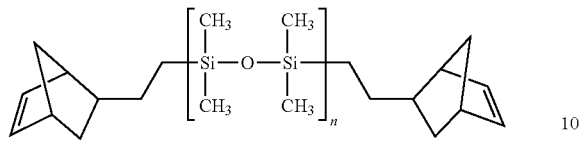
wherein n=5-5000.
* * * * *

UNITED STATES PATENT AND TRADEMARK OFFICE
CERTIFICATE OF CORRECTION

PATENT NO. : 7,683,148 B2
APPLICATION NO. : 11/428105
DATED : March 23, 2010
INVENTOR(S) : Angeletakis It is certified that error appears in the above-identified patent and that said Letters Patent is hereby corrected as shown below:

Col. 10, line 3, "norbomenyl" should read --norbornenyl--.

Col. 18, line 62, Claim 11, "norbomenyl" should read --norbornenyl--.

Signed and Sealed this

Sixteenth Day of November, 2010

David J. Kappos
*Director of the United States Patent and Trademark Office*